US012544313B2

(12) United States Patent
Roberts et al.

(10) Patent No.: US 12,544,313 B2
(45) Date of Patent: Feb. 10, 2026

(54) CLOUD-BASED MEDICATION MANAGEMENT SYSTEM AND METHOD

(71) Applicant: Connected Caregiver, LLC, Wilmington, DE (US)

(72) Inventors: Richardson Marshall Roberts, Nashville, TN (US); James McGrew, Franklin, TN (US)

(73) Assignee: Connected Caregiver, LLC, Wilmington, DE (US)

( * ) Notice: Subject to any disclaimer, the term of this patent is extended or adjusted under 35 U.S.C. 154(b) by 65 days.

(21) Appl. No.: 18/643,670

(22) Filed: Apr. 23, 2024

(65) Prior Publication Data

US 2024/0358599 A1 Oct. 31, 2024

Related U.S. Application Data

(60) Provisional application No. 63/499,071, filed on Apr. 28, 2023.

(51) Int. Cl.

*G08B 1/08* (2006.01)
*A61J 7/04* (2006.01)
*G16H 20/13* (2018.01)
*G16H 80/00* (2018.01)

(52) U.S. Cl.

CPC ........... *A61J 7/0436* (2015.05); *A61J 7/0481* (2013.01); *G16H 20/13* (2018.01); *G16H 80/00* (2018.01); *A61J 2200/30* (2013.01)

(58) Field of Classification Search

CPC .... A61J 7/0436; A61J 7/0481; A61J 2200/30; G16H 20/13; G16H 80/00; G16H 20/10; G16H 40/67

USPC .................................................... 340/539.12

See application file for complete search history.

(56) References Cited

U.S. PATENT DOCUMENTS

| | | | | |
|---|---|---|---|---|
| 10,957,436 | B1 * | 3/2021 | Aertker | A61J 1/03 |
| 2003/0036683 | A1 * | 2/2003 | Kehr | G16H 70/20 600/300 |
| 2013/0222135 | A1 * | 8/2013 | Stein | A61J 7/0481 222/23 |
| 2015/0048100 | A1 * | 2/2015 | Dickie | G16H 40/60 221/1 |
| 2015/0286852 | A1 * | 10/2015 | Sengstaken, Jr. | A61J 7/04 340/10.1 |

(Continued)

*Primary Examiner* — Tai T Nguyen

(74) *Attorney, Agent, or Firm* — Shu Chen

(57) ABSTRACT

Disclosed herein is a medication and health management system and method for assisting a caregiver to monitor medication adherence of a care recipient. An example system comprises a first computing device configured to store medications of a care recipient in a plurality of chambers, monitor the care recipient's adherence to a medication schedule via at least one sensor, and transmit measurement data of the at least one sensor to a computing server system. The computing server system is configured to process the received measurement data to determine whether any chamber has been opened for retrieval of the medications stored therein in accordance with the medication schedule of the care recipient, in response to determining that no chamber has not been opened, generate and transmit a notification signal to a second computing device of a caregiver of the care recipient to indicate a medication non-adherence event of the care recipient.

17 Claims, 6 Drawing Sheets

(56) References Cited

U.S. PATENT DOCUMENTS

| | | | | |
|---|---|---|---|---|
| 2016/0058661 | A1* | 3/2016 | Pether | A61J 7/0481 206/534 |
| 2016/0132660 | A1* | 5/2016 | Barajas | G16H 30/40 705/2 |
| 2017/0091415 | A1* | 3/2017 | Isikman | H04W 68/00 |
| 2017/0109493 | A1* | 4/2017 | Hogg | G16H 50/30 |
| 2021/0343404 | A1* | 11/2021 | Hunt | G16H 80/00 |

* cited by examiner

CLOUD-BASED MEDICATION MANAGEMENT SYSTEM AND METHOD

CROSS REFERENCE TO RELATED APPLICATION

The application claims priority to U.S. Provisional Patent Application No. 63/499,071, filed Apr. 28, 2023, entitled "CLOUD-BASED MEDICATION MANAGEMENT SYSTEM AND METHOD," the contents of which are incorporated by reference herein in its entirety.

FIELD OF TECHNOLOGY

The present disclosure generally relates to a medication management system and method, and more particularly relates to a medication and health management system and method implemented within a Cloud-based communication network.

BACKGROUND

Caregivers are an essential component of any community, as advances in medical care have brought about an increasing population which is reliant on care. Family caregivers operate as extensions of health care systems performing complex medical and therapeutic tasks and ensuring care recipient adherence to therapeutic regimens. They operate as home-based "care coordinators" and personal advocates for care recipients. As health care costs and utilization continue to rise, individuals facing physical, mental or behavioral challenges are increasingly dependent on the ability of family or other informal caregivers to operate competently as formal health care providers. Despite their important function in our society, caregivers often lack adequate training, preparation or ongoing support from health care systems.

In particular, medication use and adherence of care recipients often present a challenge of family caregivers. Non-adherence to medication regimens has become a major cause of hospital admissions, readmissions and nursing home placement for older adults. It also contributes to higher healthcare costs. Despite the fact that medications help manage illness, increase longevity and enhance quality of life, there is a noticeable absence of community-based, in-home support to help patients take their medications safely and as directed. Additionally, family caregivers, the cornerstone in providing support and assistance to aging family members, are routinely tasked with medication management for which they have no formal training.

Accordingly, there is a need for a medication and health management system and method configured to assist a caregiver to monitor medication adherence of a care recipient.

SUMMARY

Among other features, the present disclosure relates to a Cloud-based medication and health management computing system and method configured to assist a caregiver to monitor medication adherence of a care recipient. In one embodiment, the present disclosure relates to a system deployed within a Cloud-based communication network, the system comprising: a first computing device configured to store medications of a care recipient in a plurality of chambers, monitor the care recipient's adherence to a medication schedule via at least one sensor, and transmit measurement data of the at least one sensor to a computing server system. The computing server system is configured to process the received measurement data to determine whether any chamber has been opened for retrieval of the medications stored therein in accordance with the medication schedule of the care recipient, in response to determining that no chamber has not been opened, generate and transmit a notification signal to a second computing device of a caregiver of the care recipient to indicate a medication non-adherence event of the care recipient.

In one embodiment, the notification signal may comprise at least one of a text message to the second computing device used by a caregiver of the care recipient, am automated phone call to the second computing device, an alert via the application, or an email message to the caregiver. The at least one sensor may include a motion sensor configured to measure X-Y-Z axis acceleration signals of the first computing device, and the computing server system is configured to process the X-Y-Z axis acceleration signals to determine whether the one of the plurality of chambers has been opened for retrieval of the medications stored therein in accordance with the medication schedule of the care recipient.

In another embodiment, the first computing device may include a series of switches for the plurality of chambers, wherein the series of switches are connected with a common bus bar. Each of the plurality of chambers includes independent spring contacts, wherein spring contacts of the plurality of chambers are electrically connected. In one aspect, the first computing device may include at least one of a cellular module, a Wi-Fi module or a Bluetooth module configured to transmit signals to the computing server system, wherein the computing server system is cloud-based.

Further, the cloud-based computing server system may be configured to store, maintain and update a medication list of the care recipient, wherein the medication list includes information relating to a brand new of a specific prescription, active ingredients, all ingredients of the medication including non-active ingredients including binders and tablet coatings, contact details of the manufacture of the medication, how to take the medication including what to do if a patient takes too much or miss a dose, information to consider before the patient uses the medication including possible interactions with other medication or substances, safe storage and disposal information, what can happen while the patient is taking the medication including side effects, what the medication is used for, and contraindications including reasons when not to take a medication.

In yet another embodiment, the first computing device may include a plurality of light-emitting diodes and at least one speaker to generate visual and audio signals.

In another aspect, the present disclosure relates to a computer-implemented method, comprising: storing, by a first computing device deployed within a Cloud-based communication network, medications of a care recipient in a plurality of chambers; monitoring, by a processor of the first computing device, the care recipient's adherence to a medication schedule via at least one sensor; transmitting, by the first computing device, measurement data of the at least one sensor to a computing server system deployed within the Cloud-based communication network; receiving, by the computing server system, the measurement data of the at least one sensor; processing, by the computing server system, the measurement data to determine whether one of the plurality of chambers has been opened for retrieval of the medications stored therein in accordance with the medication schedule of the care recipient; in response to determining that the one of the plurality of chambers has not been opened for retrieval of the medications stored therein in accordance with the medication schedule of the care recipient, generating and transmitting, by the computing server system, a notification signal to a second computing device to indicate a medication non-adherence event of the care recipient; and receiving, by the second computing device, the notification signal.

In accordance with further aspects, the present disclosure relates to a non-transitory computer readable medium storing computer executable instructions for a system deployed in a Cloud-based communication network, the instructions being configured for: storing, by a first computing device deployed within a Cloud-based communication network, medications of a care recipient in a plurality of chambers; monitoring, by a processor of the first computing device, the care recipient's adherence to a medication schedule via at least one sensor; transmitting, by the first computing device, measurement data of the at least one sensor to a computing server system deployed within the Cloud-based communication network; receiving, by the computing server system, the measurement data of the at least one sensor; processing, by the computing server system, the measurement data to determine whether one of the plurality of chambers has been opened for retrieval of the medications stored therein in accordance with the medication schedule of the care recipient; in response to determining that the one of the plurality of chambers has not been opened for retrieval of the medications stored therein in accordance with the medication schedule of the care recipient, generating and transmitting, by the computing server system, a notification signal to a second computing device to indicate a medication non-adherence event of the care recipient; and receiving, by the second computing device, the notification signal.

The above simplified summary of example aspects serves to provide a basic understanding of the present disclosure. This summary is not an extensive overview of all contemplated aspects, and is intended to neither identify key or critical elements of all aspects nor delineate the scope of any or all aspects of the present disclosure. Its sole purpose is to present one or more aspects in a simplified form as a prelude to the more detailed description of the disclosure that follows. To the accomplishment of the foregoing, the one or more aspects of the present disclosure include the features described and exemplary pointed out in the claims.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Figure 1:
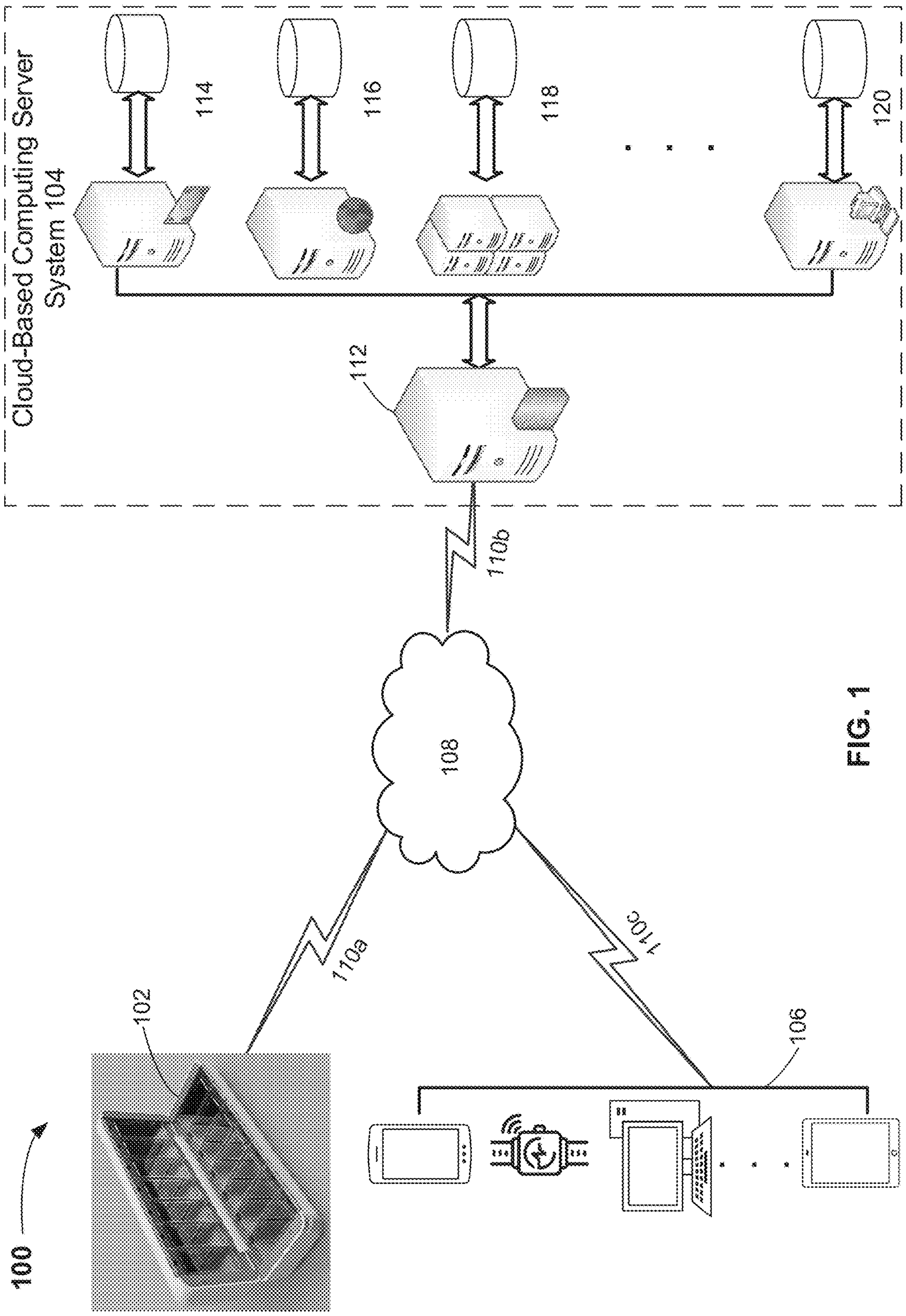
FIG. 1 illustrates a diagram of a Cloud-based medication and health management system configured to assist a caregiver to monitor medication adherence of a care recipient, according to aspects of the present disclosure.

Various aspects of the present disclosure will be described with reference to the drawings, wherein like reference numerals are used to refer to like elements throughout. In the following description, for purposes of explanation, numerous specific details are set forth in order to promote a thorough understanding of one or more aspects of the present disclosure. It may be evident in some or all instances, however, that any aspects described below can be practiced without adopting the specific design details described below.

According to aspects of the present disclosure, FIG. 1 generally illustrates a cloud-based computing system 100 comprising at least one first computing device 102, a remote cloud-based computing server system 104, and at least one second computing device 106, all deployed within a communication network 108 using suitable network connections and protocols 110*a*, 110*b*, and 110*c* to communicate with one another. Computing device 102 may be pre-filled or prepared for one or more users (e.g., care recipients) by their family caregivers pharmacies, and/or healthcare providers to store medications for the users. For example, the computing device 102 may be configured to store medication in a solid form including but not limited to tablets, capsules, powders, herbs, edibles, dietary supplements, suppositories. It should be appreciated that the computing device 102 may also be configured to contain other forms of medication, such as prepackaged liquid medicine, syrups, solutions, injectables, which may be drawn by a syringe, for example.

In accordance with aspects of the application, a user of the computing device 102 may not receive alerts if the medications are taken in a certain window (e.g., a selected time window). After that window expires, the user may receive reminders for a selected period of time. After that reminder period only then do the caregivers, or monitoring staff get notifications. For example, assuming that a medication dosage time indicates: 9:00 AM start time, 9:45 AM alert time, 10:00 AM end time, if it is detected that between 9:00-9:44:59 AM the user takes the medication, the system 100 generates no alerts or reminders, and a compliance is recorded. However, if by 9:45 AM the user has not taken the medication, one or more reminders may be generated and transmitted by the system 100 to the user and/or the caregiver or monitoring staff of the user of the computing device 102 (e.g., text messages, emails, phone calls, etc.). If the user takes the medications between 9:45 and 9:59:59 AM, the reminders stop and the system 100 records a compliance. If the user has not taken the medications by 10:00 AM, then a non-compliance is registered, and an alert is generated and transmitted to the caregiver, or monitoring staff who can contact the user of the computing device 102 and ensure the medications are taken. If they manage to get the user to take the medications, then they can record a compliance.

As will be described fully below, the computing device 102 may be programmed to monitor a care recipient's adherence to a medication schedule and an alert or notification may be generated by the remote cloud-based computing server system 104 in response to detecting a medication non-adherence event or pattern of the care recipient. For example, the server system 104 may detect that one of the medication chambers of the computing device 102 remains full past a scheduled dose time or time period, a notification may be generated and transmitted to at least one second computing device 106 used by the caregiver or healthcare provider of the care recipient. For example, the notification may include but not limited to a text message, an automated phone call to the caregiver or healthcare provider. Further, a visual alert via patterns of LED lighting on the computing device 102, and/or an audio alert via speaker(s) on the computing device 102 may be implemented to remind the care recipient.

In a preferred embodiment, the computing device 106, which is used by a caregiver of the care recipient, may comprise at least one of personal computers, laptops, tablets, mobile devices, smart phones, smart watches, wearable electronics, cellular devices, smart home devices, virtual or augmented reality devices. For example, the computing device 106 may have a mobile or web-based application (e.g., native iOS or Android apps) downloaded and installed thereon to monitor the care recipient's adherence to a medication schedule and receive a notification in real-time in response to detecting a medication non-adherence event or pattern of the care recipient. In another embodiment, the application may be downloaded and installed on a selected computing device of the user of the computing device 102.

It should be appreciated that, in other embodiments, the cloud-based computing server system 104 of the present disclosure may be configured to enable communications between the computing device 102 and other computing devices accessible by a guardian, family, close friends, trusted individuals, insurance providers and/or healthcare providers (e.g., physicians, nurses, assistants, and pharmacists) of the user of the computing device 102, for example. That is, the care community of the user may have access to information about the adherence of the patient to their medication schedule, including receiving notifications and other monitoring information. In some embodiments, the caregiver and/or the healthcare providers of the user of the computing device 102 may edit medication schedules to accommodate changes in dosage and medication regimen.

A communication network (e.g., communication network 108) may refer to a geographically distributed collection of computing devices or data points interconnected by communication links and segments for transporting signals and data therebetween. A protocol (e.g., protocols 110*a*, 110*b*, and 110*c*) may refer to a set of rules defining how computing devices and networks may interact with each other, such as frame relay, internet protocol (IP), transmission control protocol (TCP), user datagram protocol (UDP), hypertext transfer protocol (HTTP). Many types of communication networks are available, ranging from local area networks (LANs), wide area networks (WANs), cellular networks, to overlay networks and software-defined networks (SDNs), a packet data network (e.g., the Internet), mobile telephone networks (e.g., cellular networks, such as 4G or 5G), Plain Old Telephone (POTS) networks, and wireless data networks (e.g., Institute of Electrical and Electronics Engineers (IEEE) 802.11 family of standards known as Wi-Fi®, WiGig®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, virtual private networks (VPN), Bluetooth, Near Field Communication (NFC), or any other suitable network. Computing devices deployed with the communication network 108 may be configured to communicate in a peer to peer manner to replace, duplicate, supplement or extend the functionalities of communication network 108.

System 100 of the present disclosure employs a cloud-based communication network 108 for providing computing services using shared resources. Cloud computing may generally include Internet-based computing in which computing resources are dynamically provisioned and allocated to each connected computing device or other devices on-demand, from a collection of resources available via the network or the cloud. Cloud computing resources may include any type of resource, such as computing, storage, and networking. For instance, resources may include service devices (firewalls, deep packet inspectors, traffic monitors, load balancers, etc.), compute/processing devices (servers, CPUs, GPUs, random access memory, caches, etc.), and storage devices (e.g., network attached storages, storage area network devices, hard disk drives, solid-state devices, etc.). In addition, such resources may be used to support virtual networks, virtual machines, databases, applications, etc.

Cloud computing resources accessible via communication network 108 may include a private cloud, a public cloud, and/or a hybrid cloud. For example, a private cloud may be a cloud infrastructure operated by an enterprise for use by the enterprise, while a public cloud may refer to a cloud infrastructure that provides services and resources over a network for public use. In a hybrid cloud computing environment which uses a mix of on-premises, private cloud and third-party, public cloud services with orchestration between the two platforms, data and applications may move between private and public clouds for greater flexibility and more deployment options.

In accordance with an aspect, computing server system 104 of the present disclosure may be cloud-based and may comprise at least one of personal computers, servers, server farms, laptops, tablets, mobile devices, smart phones, smart watches, fitness tracker devices, cellular devices, gaming devices, media players, network enabled printers, routers, wireless access points, network appliances, storage systems, gateway devices, smart home devices, virtual or augmented reality devices, one, a portion of a plurality, or a plurality of devices 102, one, a portion of a plurality, or a plurality devices 106, or any other suitable devices that are deployed in the same or different communication network of computing devices 102, 106. As will be described fully below, computing server system 104 may be configured to provide functionalities for any connected devices such as providing requested services, sharing data or provisioning resources among multiple client devices, or performing computations for each connected client device.

In one embodiment, computing server system 104 may implement a management computing device/interface 112 configured to process, transform and exchange various information obtained from disparate data sources 114, 116, 118, 120 (3$^{rd}$ party and/or proprietary to the system 100), including bi-directional data exchange and automation of task workflows, to create a seamless member experience. It should be appreciated that data storage capacity, processing power and networking of the computing server system 104 may all be scaled (e.g., increasing or decreasing various information technology (IT) resources as needed to meet changing demand) using the cloud computing infrastructure disclosed in accordance with the present disclosure. For example, the cloud-based computing server system 104 may be scaled vertically by adding or subtracting power to an existing cloud server by upgrading random access memory (RAM), storage or processing power (e.g., central processing unit (CPU)). This type of scaling may have an upper limit based on the capacity of a specific server or machine being scaled and scaling beyond that may require downtime. Further, the Cloud-based computing server system 104 may be scaled horizontally by adding more servers (e.g., servers) to distribute workload across machines, which in turn increases performance and storage capacity. This type of scaling may require minimal downtime. In addition, the Cloud-based computing server system 104 may be configured to grow or shrink dynamically in response to changing workload demands, such as a sudden spike in Internet traffic. Such elasticity of the cloud-based computing server system 104 may automatically adapt to match resources with demand as closely as possible in real time. For example, when the system 100 experiences variable and unpredictable workloads (e.g., a sudden increased number of computing devices 102, 106 deployed within the system 100), the cloud-based computing server system 104 may be configured to scale virtual infrastructure in the cloud computing environment for the system 100 for additional computing resources.

Figure 2:
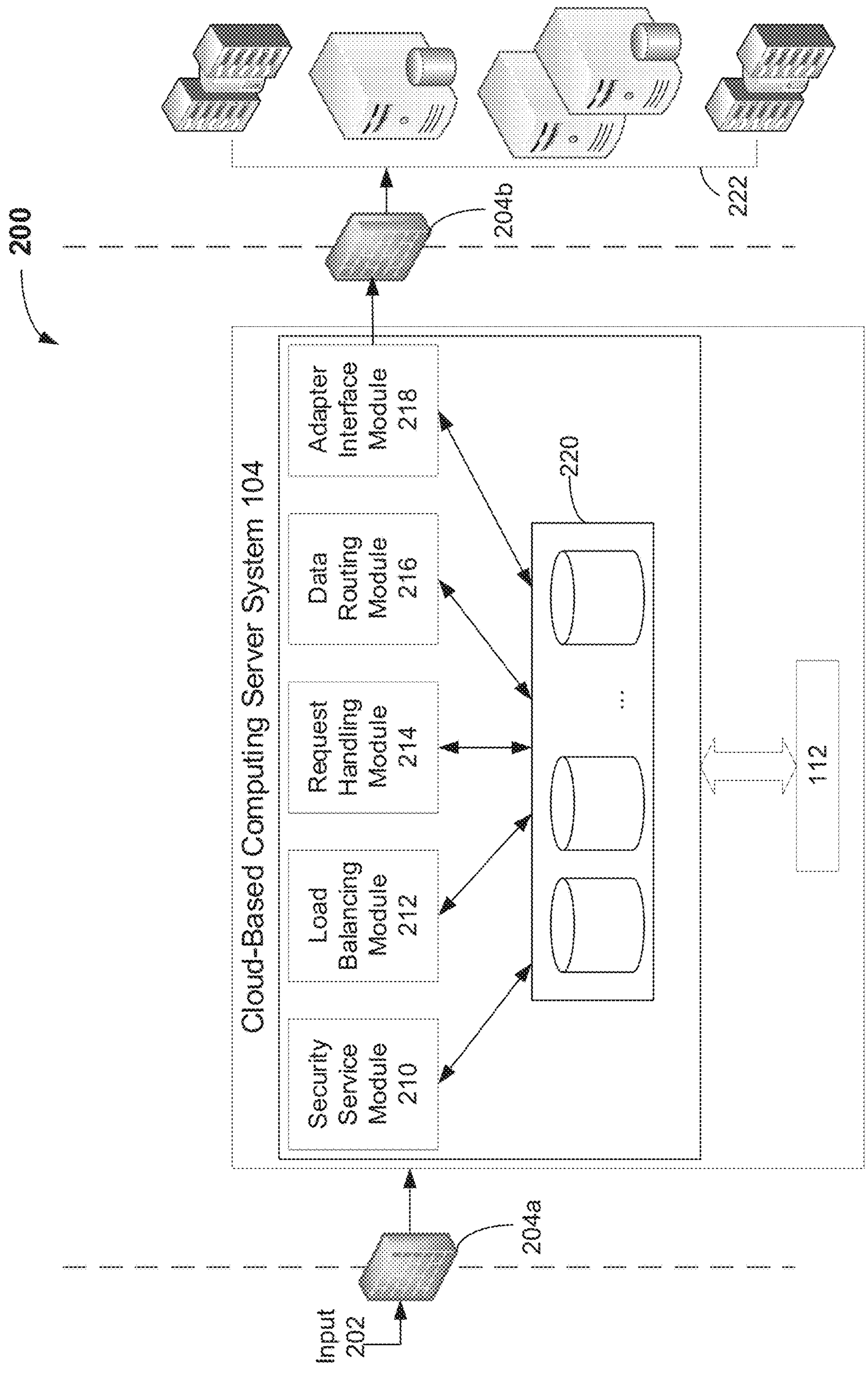
FIG. 2 illustrates a diagram of a Cloud-based management server system, according to aspects of the present disclosure.

FIG. 2 shows an example architecture 200 of the system 100 of FIG. 1 using a cloud-based computing server system 104 for exchanging information among different entities, according to aspects of the present disclosure. On a high level, the cloud-based computing server system 104 facilitates on-demand delivery of compute power, database storage, software applications, and other IT resources through a cloud services platform via the Internet. The cloud-based computing server system 104 may include multiple cloud servers concurrently running on a hypervisor to control the capacity of underlying operating systems and allocate processor cycles, memory space, network bandwidth and so on. Input 202 (e.g., data and messages) to the cloud-based computing server system 104 may be obtained from devices 102, 106, or other data sources or computing devices connected therewith. In one embodiment, input 202 may include cloud service invocation messages, result messages, request messages, or any messages communicated among different cloud computing devices. For example, a message may include a message type (e.g., a type value from a set of shared type constants), a unique identifier (e.g., an identifier used to correlate this message with one or more other messages), priority information to support for priority based message queues, timeout, sensitivity indicator to support message data isolation, message source (e.g., a uniform resource identifier (URL) of a sender), a message destination (e.g., a URL that uniquely identifies the destination), a request context (e.g., request information from a dispatcher), and/or a message payload. The payload may have different attributes depending upon the type of message that is being sent, such as parameter data and result data.

The cloud-based computing server system 104 may be configured to operate as a secure intermediary computing environment for real time or near real time data collection, storage, and analysis in connection with the use of devices 102, 106. For example, server system 104 may implement techniques to facilitate communications among various mobile computing devices and cloud computing entities (cloud datacenters, cloud web servers, cloud application servers, cloud database servers, cloud storage devices) despite their incompatibilities in communication, such as differences between formats or communication protocols. In certain embodiment, server system 104 may be configured to translate communication protocols among different computing devices. For example, in response to receiving the input 202 from the devices 102, 106, the management computing device/interface 112 may be configured to handle protocol translation, service discovery, basic business logic, authentication and security policy enforcements, stabilization and load balancing, cache management and various monitoring, logging and analytics functions. In one embodiment, the management computing device/interface 112 may be an external endpoint made available to consumers of various services provided by the system 100, and may encapsulate the business functionality of the overall architecture of the system 100. For example, the management computing device/interface 112 may include at least one application programming interface (API) gateway device which may function as a common entry point for some or all clients (desktop, mobile, tablet or hubs (e.g., computing devices deployed within the system 100 and connected with any of 102, 106, 114, 116, 118, and 120) accessing various resources and services provided by the system 100.

Server system 104 may be implemented using hardware, software, firmware, or combinations thereof. For example, the cloud-based computing server system 104 may include one or more computing devices, such as a server computer, one or more memory storage data repositories 220, one or more processors, and operate with different kinds of operating systems. Each memory storage device may implement one or more databases (e.g., a document database, a relational database, or other type of database), one or more file stores, one or more file systems, or combinations thereof, and may include instructions stored thereon which, when executed by the processor(s), cause the processor(s) to implement one or more operations disclosed herein.

Data repositories 220 may be accessible by various modules 210-218. For example, one of the data repository 220 may store all the metadata (e.g., run-time and design-time data, each having their own requirements on availability and performance) associated with the server system 104. A tenant or subscriber (e.g., device 102 or 106) of the server system 202 may have any number of applications installed thereon. Each application may be versioned and have at least one versioned resource API, and corresponding versioned service. The data repository may store one or more callable interfaces, which may be invoked by device 102, 106. The callable interface may be implemented to translate between a one format, protocol, or architectural style for communication and another format, protocol, or architectural style for communication. Further, another data repository 220 may be used to store information about processing occurring in the cloud-based computing server system 104, such as messages communicated via the server system 104 and log information. Additional data repositories 220 may be configured to store logging and analytics data captured during processing in the cloud-based computing server system 104. Depending on the demand of computing devices seeking to communicate with backend cloud resources 222, the cloud-based computing server system 104 may be configured to handle surges and temporary periods of higher than normal traffic between each connected computing device and other cloud computing devices. For example, the cloud-based computing server system 104 may include elements that support scalability such that components may be added or replaced to satisfy demand in communication.

Input 202 (e.g., a request for cloud service) may be communicated between device 102 or 106 and the cloud-based computing server system 104 via one or more callable interfaces, e.g., APIs. The cloud-based computing server system 104 may be protected by one or more firewalls 204*a*, 204*b* to provide a secure environment to process requests from various computing devices. For example, firewalls 204*a*, 204*b* may permit communication of messages between the cloud-based computing server system 104 and each device 102 and/or 106. Such messages (e.g., SPDY messages, hypertext transfer protocol (HTTP) messages or representational state transfer (REST) messages) may conform to a communication protocol (e.g., SPDY, HTTP, or REST). Input 202 that is received through the firewall 204*a* may be processed first by security service module 210 which is configured to manage security authentication for a user associated with a service request by at least restricting access to only those who have the required credentials to certain medical data of a care recipient and/or family caregiver. In one embodiment, security authentication may be determined for a request, a session, a user, a device, other criterion related to the user, or combinations thereof. Security authentication may be performed for each request that is received or based on a previous verification of a request. Security authentication may be determined for a user or a device, such that requests to different cloud services 222 may be authenticated based on a single verification of security.

Upon determining security authentication, the cloud-based computing server system 104 may use the load balancing module 212 to detect to which cloud service 222 the received request is directed, and use a request handling module 214 to transmit each service request to an appropriate cloud service 222. A request may be routed to an appropriate service 222 upon dispatch, or to another module of the cloud-based computing server system 104. The request handling module 214 may resolve a request to determine its destination based on a location (e.g., a URL of the request). The request handling module 214 may parse a request's header to extract one or more of the following information: tenant identifier, service identifier, application name, application version, request resource, operation and parameters, etc. The request handling module 214 may use the parsed information to perform a lookup in data repositories 220 and retrieve corresponding application metadata. The request handling module 214 may determine the target service based on the requested resource and the mappings in the stored metadata. Via formatting the request and any other necessary information, the request handling module 214 may place the input message on data routing module 216 for further processing, or on a queue and await the corresponding response. The request handling module 214 may process responses received from the data routing module 216 and return a response to, e.g., the device 102 and/or 106.

The data routing module 216 may manage delivery of messages to destinations registered with itself. The data routing module 216 may operate as a central system for managing communications in cloud services 222, such that additional centralized services (additional authorization, debugging, etc.) may be plugged in as necessary. Data captured by the data routing module 216 may be stored in the data repositories 220.

The data routing module 216 may route messages to one or more destinations 222 directly, or with the aid of an adapter interface module 218 by translating or converting a message to a protocol supported by a receiving cloud device. The adapter interface module 218 may establish separate communication connections with each of cloud resources 222.

In accordance with aspects of the present disclosure, the cloud-based computing server system 104 may be configured to obtain real time data from devices 102, 106, and/or other data sources, such as stored historical data, conducting data capture, storage, analysis, search, sharing, transferring, querying, and updating of the obtained data using proprietary algorithms, and providing feedback to e.g., a caregiver or a medical practitioner in a real time, near real time, daily, monthly, or at a user requested interval to enhance medication adherence of the care recipient. The data may also be used to predict behavior or health outcomes to enhance care.

Figure 3:
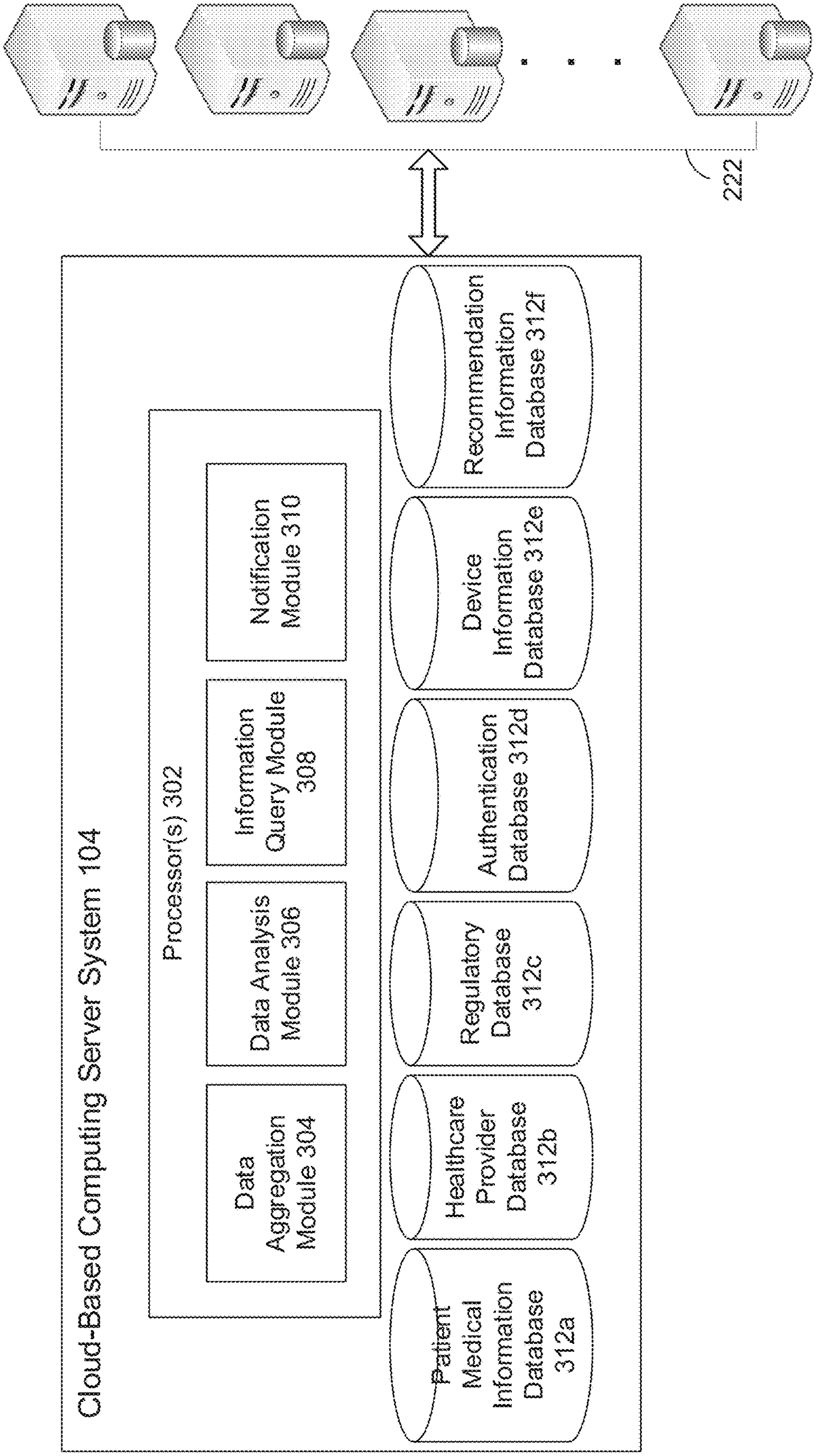
FIG. 3 illustrates another diagram of the Cloud-based management server system of FIG. 2, according to aspects of the present disclosure.

Referring to FIG. 3, the cloud-based computing server system 104 may include one or more processors 302 communicatively coupled to a plurality of information databases 312*a*-312*f*. The server system 104 may also be configured to access the plurality of servers and cloud-implemented processing, memory, and data resources 222 connected with the underlying cloud-based computing server system 104 shown in FIG. 2. Thus, as information dynamically changes, the server system 104 may be configured to scale with additional processing resources, server resources, data storage resources, and data management resources.

Databases 312*a*-312*f* may include a plurality of example database(s), database management system(s), server(s) to facilitate management, provision, transfer, and analysis of various patient healthcare information. For example, database 312*a* may retain any confidential or publicly available medical information of a particular care recipient collected from various data sources by a data aggregation module 304. Example medical information may include, but not limited to, any information on the care recipient's health conditions, medical conditions, characterizations, assessments, test results, biographical or demographical information, prescription information, immunization records, care services provided, insurance policy information, coverage/benefits guidelines/rules for care services, healthcare plans, explanations of benefits, and the like.

Further, information database 312*b* may retain any relevant information related to various healthcare or services providers (e.g., physicians, nurses, pharmacists, or labs). The provider information may include, but not limited to, provider identification information, provider location, amenities offered by providers, provider schedule information, technology offered by providers, preventive/curative/palliative/other care service offerings information, in-network/preferred provider information, advertising information, provider billing information, reviews of providers, provider feedback, and the like.

Moreover, information repository 312*c* may retain relevant health information regulatory rules. The regulation information may include, but not limited to, regulations issued by a government authority, such as the Departments of Health and Human Services, Labor, and Treasury that require insurance plans/issuers to cover certain preventive services delivered by in-network providers without any cost-sharing. The regulation information may also include information relating to Health Insurance Portability and Accountability Act of 1996 (HIPAA) regulatory policies, procedures, and guidelines for controlling and maintaining privacy/security of confidential health information.

As the care recipient's medical information and regulatory information exchanging among different entities, database 312*d* may retain relevant authentication information to facilitate privacy and security for data accessing and transferring. For example, the authentication information may restrict or grant access to certain care recipient's confidential health and/or other system-provided features via various communication interfaces.

In accordance with aspects of the present disclosure, a device information database 312*e* may be configured to obtain and store real-time data from at least devices 102 and 106 of FIG. 1, determine relativeness of data received from devices 102, 106 and from other sources, and exchange information with other modules or computing devices via appropriate interfaces.

Moreover, a recommendation information database 312*f* may be configured to encode knowledge extracted from various sources of medical expertise in a number of rule sets including artificial intelligence oriented systems and technologies. Knowledge here refers to a representation that resembles the way experts tend to express most of their problem solving techniques. The recommendation information may include text, audio, video, and other rich media explanations to caregivers or health providers.

As shown in FIG. 3, the cloud-based computing server system 104 may include one or more processor(s) 302 configured to control and execute a number of modules including a data aggregation module 304, data analysis module 306, information query module 308, and notification module 310.

More specifically, the data aggregation module 304 may be configured to utilize one or more communication interfaces to access one or more of the databases 312*a*-312*f*, and/or the other data source(s) 220 through appropriate network connections, determine a degree of reliability, consistency, comprehensiveness, thoroughness, and accuracy of obtained information corresponding to a specific patient, and aggregate the obtained information using appropriate data structures for further data storage or processing. For example, the data aggregation module 304 may access manifold sets of confidential health information that corresponds to a specific care recipient from various data sources. Such date aggregation may include organizing, categorizing, qualifying, and comparing different sets of information; detecting, identifying, and handling errors and discrepancies. Thus, the data aggregation module 304 may be configured to store the aggregated information regarding at least one care recipient and the corresponding caregiver information in one or more of the databases 312*a*-312*f*.

Moreover, the data aggregation module 304 may acquire and store authentication information in the authentication database 312*d*. For example, a user (e.g., a care recipient), a family caregiver, a legal representative, or a healthcare provider, may use an interface of a computing device to seek access to the user's confidential health information with a set of credentials. The authentication information, which may be of any suitable form and content, may be retrieved and used to check the credentials provided. Pursuant to authentication, the user may be granted access to at least a portion of the stored information in databases 312*a*-312*f* corresponding to the identified patient.

In one aspect, the data aggregation module 304 may be linked to a remote server (e.g., one of 222) that provides updates on information changes in databases 312*a*-312*f* corresponding to the identified care recipient, periodically crawl for updates and changes, or may otherwise receive notice of information changes from other data sources. Thereafter, the data aggregation module 304 may process the changes to identify the content and scope of the changes, and potential ramifications. For example, the data aggregation module 304 may correlate the changes with stored care recipient's information, determine that the changes affect prior system feedback, and determine that the changes translate to greater or lesser thresholds for various personalized, up-to-date recommendations to support, e.g., a care recipient's medication regime. As will be described fully below, the data analysis module 306 may utilize information stored in databases 312*a*-312*f* for situation analysis and implement a number of rules to generate alerts, notifications and/or recommendations to the caregiver of the care recipient. For example, using knowledge representation and reasoning, the information stored in databases 312*a*-312*f* is semantically linked and formally structured by the data aggregation module 304, such that the data analysis module 306 may be configured to analyze new information additions in databases 312*a*-312*f* and changes in rules from experts and automatic learning, perform information changes, and propagate the changes to relevant modules. After each change implementation, the data analysis module 306 may log and maintain these changes for later audit purposes including change recovery and for understanding the evolution history of the rules.

To ensure accuracy and relevancy of each recommendation, the data analysis module 306 may assess information relating to a recommendation rule set and assign a weight to the information. For example, missing information may have a lower score than non-missing information. Information may be weighted according to its data source. That is, information obtained from a healthcare provider may be weighted higher or lower relative to information provided by a care recipient; information collected from devices 102, 106 may be considered more reliable than corresponding or conflicting information self-reported by the care recipient. Based on the assigned weight, one or more follow-up questions prompting for further information or clarifying information may be generated by an information query module 308.

The information query module 308 may be configured to handle feedback received from e.g., caregivers or health providers in order to search, retrieve, modify, or facilitate transfer of particular information among different modules and information repositories.

Notification module 310 may be configured to generate and deliver an alert based on user preferences through one or more channels, detect user responses, and take further actions based on the responses. Some alert channels may include known communication resources, either one-way or two-way. Examples include SMS, Twitter, push notifications, and Google Cloud Messaging.

It should be appreciated that although the deployment and implementation of the system 100 has been described as a cloud-based computing environment, the present disclosure may be used in other appropriate computing contexts including but not limited to fog computing, edge computing, mesh computing, on-perm hosting, and colocation hosting.

Figure 4:
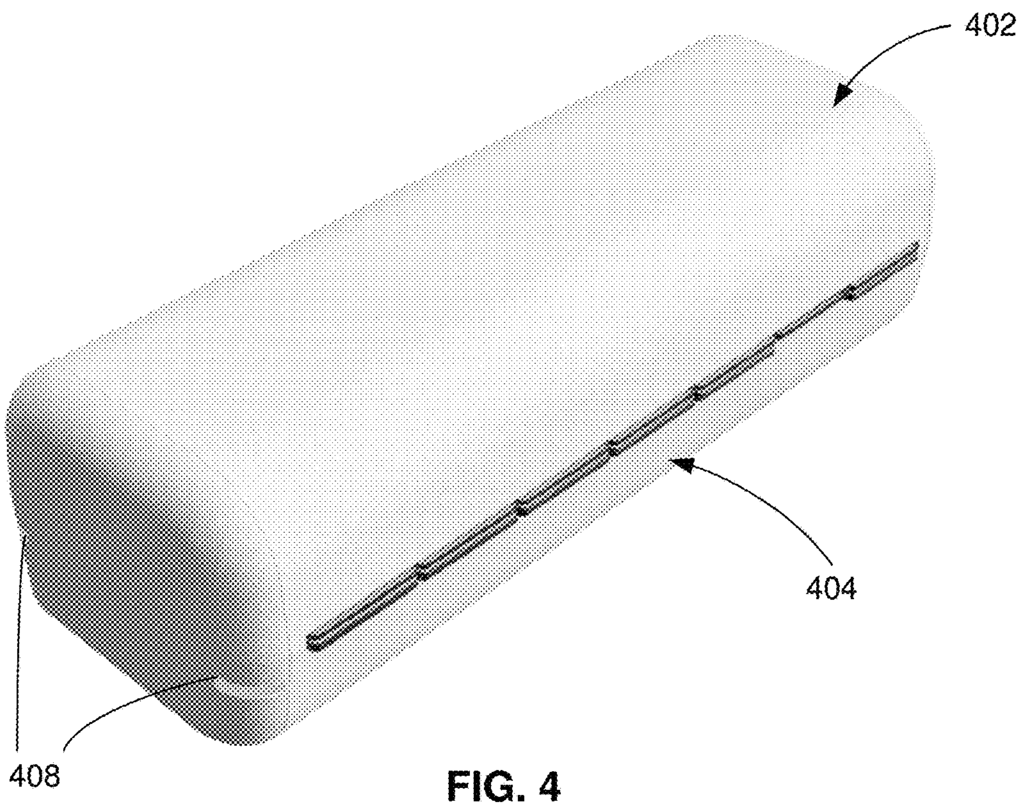
FIG. 4 illustrates a perspective view of a computing device in a completely closed state for storing medications of a care recipient, according to aspects of the present disclosure.
Figure 5:
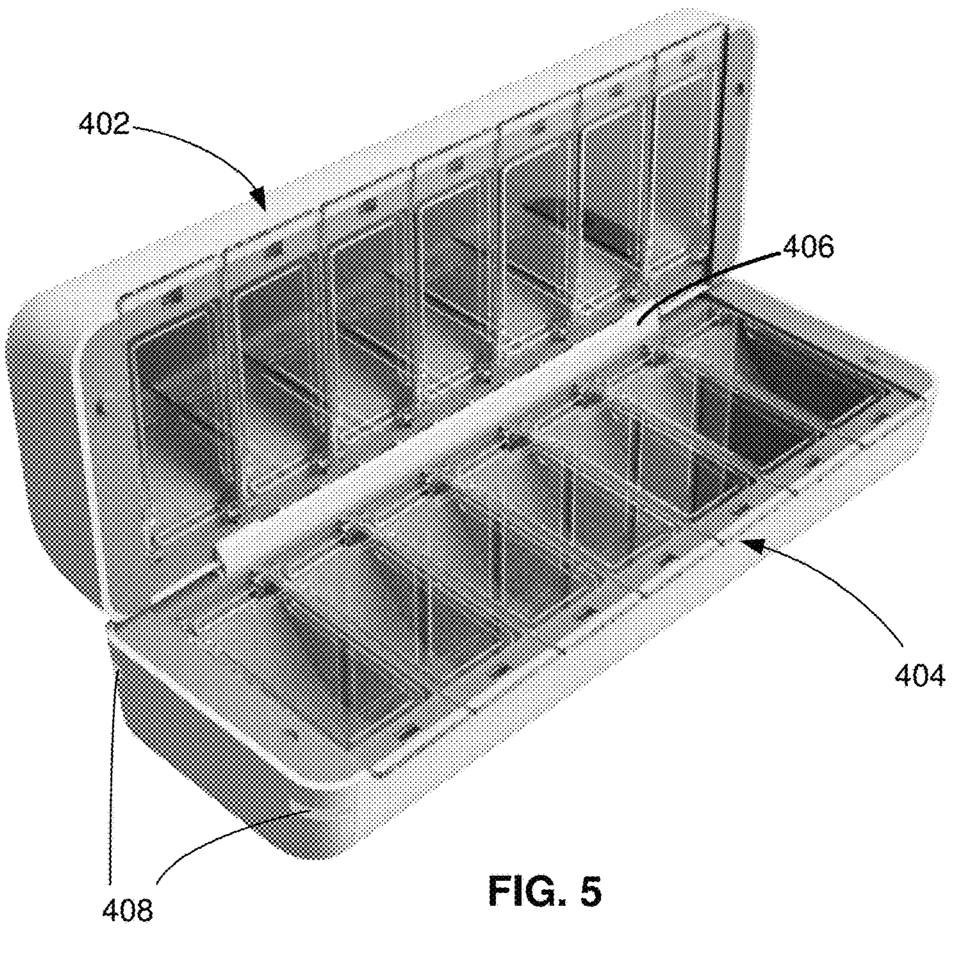
FIG. 5 illustrates a perspective view of a computing device in a half-open state for storing medications of a care recipient, according to aspects of the present disclosure.
Figure 6:
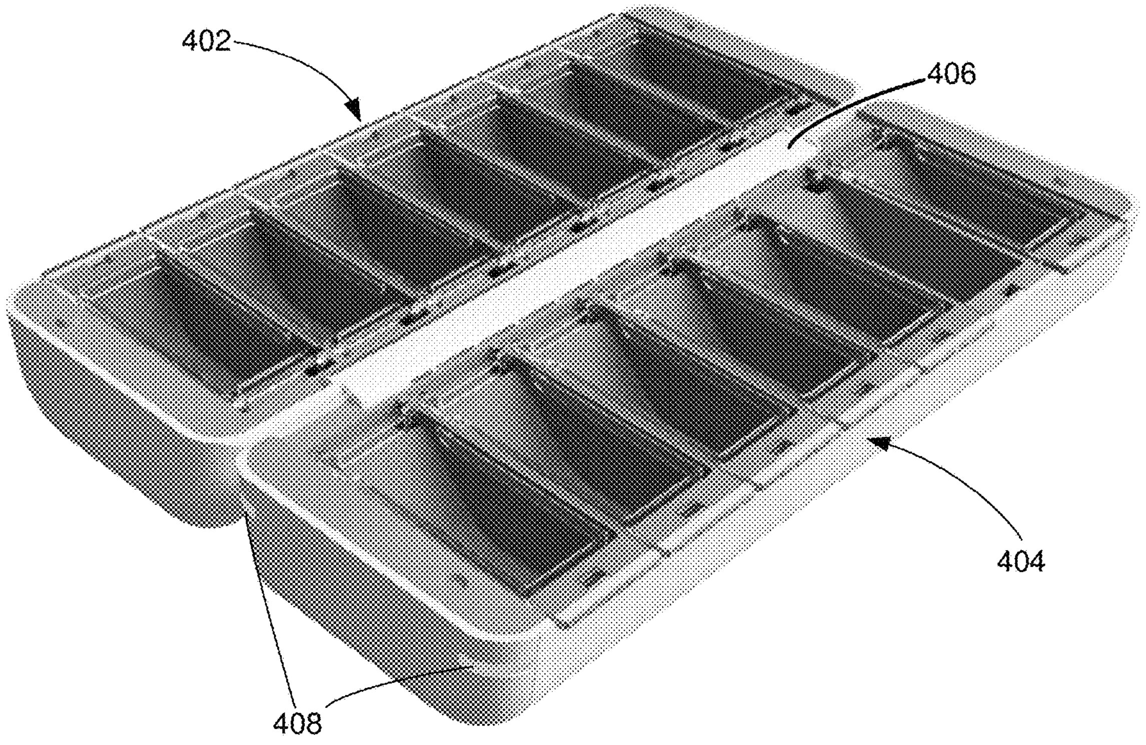
FIG. 6 illustrates a perspective view of a computing device in a completely open state for storing medications of a care recipient, according to aspects of the present disclosure.
Figure 7:
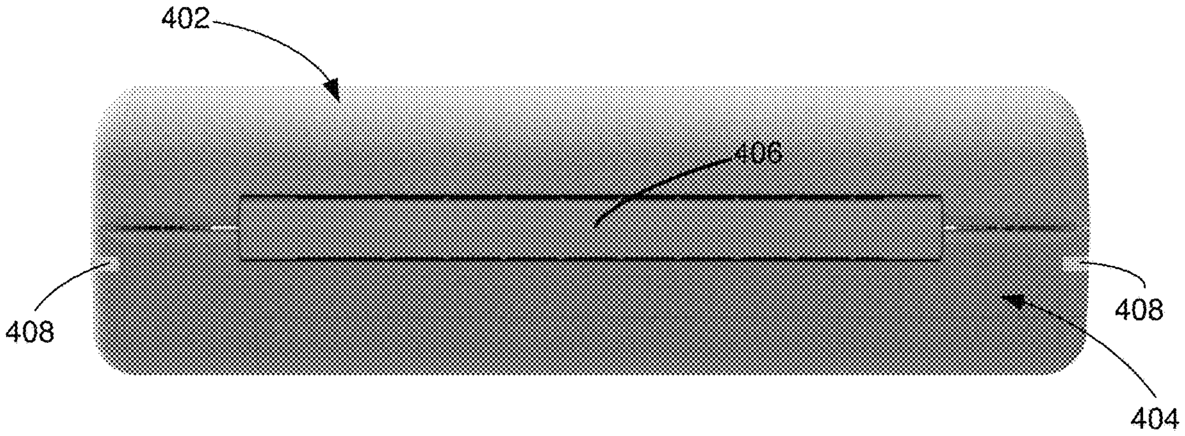
FIG. 7 illustrates a back view of a computing device in a completely closed state for storing medications of a care recipient, according to aspects of the present disclosure.
Figure 8A:
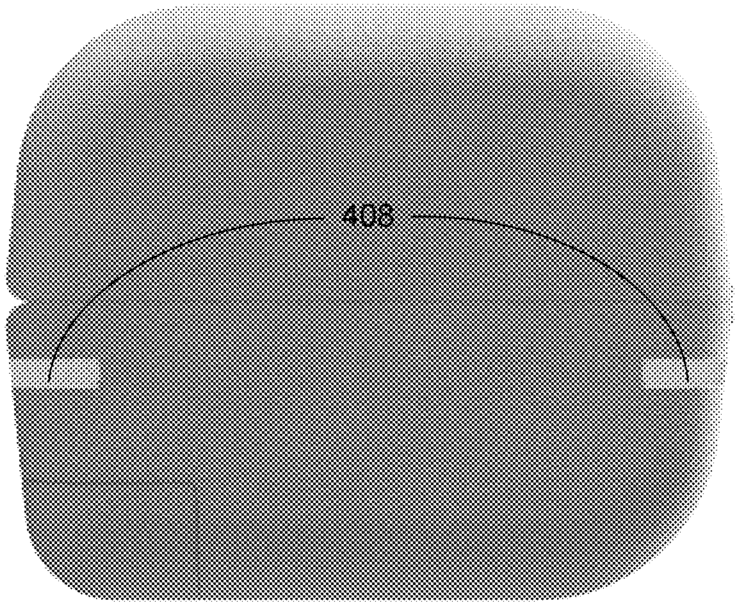
FIGS. 8(A) and 8(B) respectively illustrate a side view of a computing device in a completely closed state for storing medications of a care recipient, according to aspects of the present disclosure.
Figure 8B:
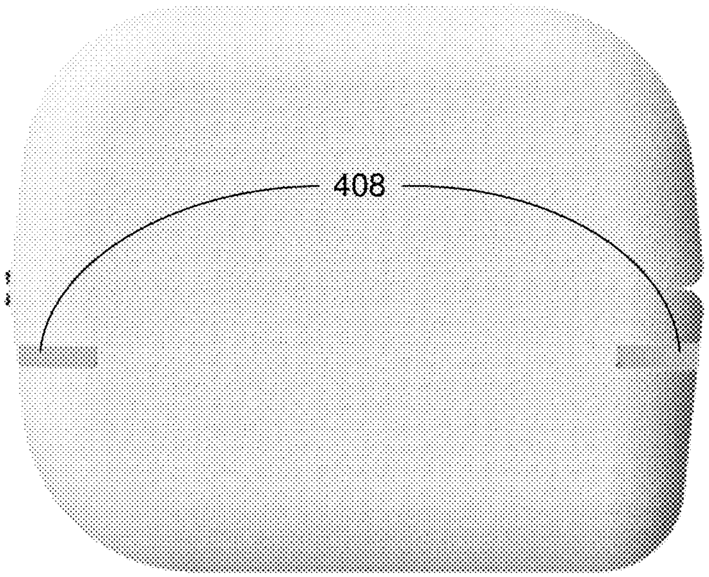

FIGS. 4, 5 and 6 illustrate the computing device 102 of the present disclosure in a complete closed state, a half-open state (90° between the two halves 402, 404 of the computing device 102) and a completely open state (180° between the two halves 402, 404 of the computing device 102), respectively. In one embodiment, the computing device 102 may generally have a clamshell design-a one-piece structure (when completely closed) including two halves 402, 404 joined by a hinge 406 that runs lengthwise on the back of the computing device 102, as shown in FIGS. 5-7, which allows the two halves 402, 404 to move relative to each other. In one embodiment, the length of the hinge 406 may be less than the length of the computing device 102 (70% of the length of the computing device 102). As shown in FIGS. 4-7, 8(A) and 8(B), four light-emitting diodes (LEDs) may be respectively implemented on the corners of the computing device 102 to generate visual alerts to a user in accordance with a selected pattern (e.g., flashing green light).

In accordance with aspects of the present disclosure, the computing device 102 may include a number of individual chambers for storing medications of a user. In one example, as shown in FIGS. 5 and 6, each half 402, 404 of the computing device 102 may respectively contain 7 chambers such that a user may manage his/her medications on a weekly basis. In another embodiment, the computing device 102 may be configured to include more (e.g., more rows per half 402, 404) or less chambers to accommodate different medication schedules of a specific user.

In order to detect whether the medications stored in one of the chambers have been taken by the user, one or more motion sensors may be implemented on the computing device 102. In one embodiment, the motion sensor measurement results may be obtained and transmitted by the computing device 102 to the cloud-based computing server system 104 which may be configured to run at least one oscillation detection algorithm to detect whether a medication chamber has been opened by the user. For example, such a motion sensor may include an accelerometer (e.g., 1-axis, 2-axis, 3-axis or multi-axis accelerometer, gyroscopes or any suitable sensor) to detect a motion of the computing device 102 against a predetermined threshold. In a preferred embodiment, the motion sensor includes at least one micro electro mechanical system (MEMS) sensor (3-axis accelerometer) disposed within the computing device 102 and configured to detect X-Y-Z axis acceleration signals of the computing device 102 when a user of the computing device 102 opens one of the chamber to remove the medication(s) stored therein. A heat source, surrounded by thermopiles in the silicon chip of the sensor, is suspended across a cavity. This heat source creates a field of heated gas around it, commonly referred as hot air bubble. The thermopiles of the sensor may detect changes in the temperature field around the heater. In one aspect, applied acceleration to the computing device 102 may disturb the temperature profile of the sensor. The temperature, and hence voltage output of thermopiles may then be different. The differential voltage at the thermopile outputs may be directly proportional to the acceleration. A signal path on the sensor may be configured to measure accelerations of the computing device 102 at three directions (X-Y-Z axis) and temperature sequentially.

Further, a series of normally open switches for all the chambers of the computing device 102 may be constructed with a common bus bar. Independent spring contacts for all the chambers may be electrically connected. This provides a series of switches that appear to the user to operate independently but obscure which switch a user activated.

It should be appreciated that, in order to determine whether a user of the computing device 102 opens one of the chambers to take the medication(s) stored therein, the computing device 102 may use other technologies including but not limited to weight sensors, pressure sensors, chemical sensors, or optical sensors. For example, the computing device 102 may include electronics to detect a sufficient change in the average dielectric constant of the volume of a chamber to detect a removal of medication from that chamber (i.e., capacitance sensing).

In accordance with aspects of the present disclosure, the computing device 102 may comprise a cellular module and/or a Wi-Fi module configured to transmit signals (e.g., measurement data from various sensors) to other computing devices deployed within the system 100 (e.g., the computing device 106, the cloud-based computing server 104, etc.). Further, a Bluetooth module may also be implemented to communicate with a Bluetooth enabled device separate from the computing device 102 (e.g., the computing device 106). It should be appreciated that other communications technologies may also be used such as BLE, ZigBee, Ethernet, etc.

In another aspect, the computing device 102 may use a battery module (not shown) to power various electronics included therein. In one embodiment, such a battery module may be configured to be rechargeable via a battery charging circuit connecting the battery to electrical interfaces for charging. Interfaces for powering the battery charging circuit may include wall sockets, barrel plugs, USB cables, micro-USB, or custom chargers, for example. The battery may be a single cell, such as a AA, AAA, 9-volt, lithium ion. The battery may also comprise multiple cells (e.g., 3×AA batteries) in series and/or parallel to deliver the amount of power appropriate for the functions described herein. Since the various circuits described in the electronics may require specific voltages in order to operate, the battery output may be connected to one or more voltage regulators to supply the appropriate voltage(s) to the respective circuits. In one aspect, a microcontroller of the computing device 102 may control the battery charging circuit to charge the battery when the computing device 102 is plugged into a power source. The microcontroller may control the charging pattern of the battery of the computing device 102. For example, the battery may be programmed to sleep at preprogrammed times to reduce overall power consumption and improve battery life.

In accordance with aspects of the present disclosure, the remote cloud-based computing server system 104 may be configured to store, maintain and update a medication list of a specific care recipient. Such a list may include information relating to the brand new of a specific prescription, active ingredient(s), all ingredients of the medication including non-active ingredients (e.g., binders, tablet coatings), contact details of the manufacture of the medication, how to take the medication including what to do if a patient takes too much or miss a dose, information to consider before the patient uses the medication including possible interactions with other medication or substances, safe storage and disposal information, what can happen while the patient is taking the medication including side effects, what the medication is used for, and contraindications including reasons when not to take a medication.

As will be described fully below, a caregiver may use e.g., at least one computing device 106 to access the system 100 and set up configurable alerts to monitor (e.g., text, phone, app alerts, etc.) medication adherence of a care recipient who is using the computing device 102 for medication management purposes. In one aspect, configurable targets, people, methods, times may be set up. Further, the caregiver may set up configurable standards for accepting an interaction as valid.

In one example, the computing device 102 may include 14 chambers, such that a user may use the computing device 102 as a bi-weekly medication organizer. In one aspect, each chamber may be configured to include one or more separation parts to further partition each chamber into more portions for storing, e.g., medications that may need to be taken during different times during a day. The user may also receive or pick up a pre-loaded computing device 102 from pharmacies and other facilities with machines to automatically sort and move pills, and these machines may be used to place the appropriate medications into the chambers of the computing device 102. For example, a device (not shown) in the pharmacy or other facility may be connected to a computer and controlled by the remote cloud-based computing server system 104 which may dispense medications into the computing device 102 in accordance with a medication list of a specific patient. An App (e.g., native iOS or Android Apps) may obtain data related to the patient's medication regimen to the computer. The computer may then map the day-of-week and time-of-day data related to the patient's medication regimen to the chambers of the computing device 102 to be filled.

As discussed above, the computing device 102 may use the microprocessor and various sensors to detect X-Y-Z axis acceleration signals of the computing device 102. The sensor measurement results may be transmitted by the computing device 102 to the cloud-based computing server system 104 which may be configured to run at least one oscillation detection algorithm to detect whether a medication chamber has been opened by a user. In one embodiment, the microcontroller of the computing device 102 may perform coarse filtering on the received sensor data and send the data to the cloud-based computing server system 104 for further analysis via a cellular module or a Wi-Fi module.

In accordance with aspects of the present disclosure, if a care recipient has not taken his/her medications within a permissible window of time near the prescribed time according to his/her medication schedule saved on the cloud-based computing server system 104, a notification may be generated via the one or more selected modes of communications, such as by a text message, automated phone call, email message, App alert, etc., to at least one caregiver of the care recipient. For example, text messages may be sent via the cellular network.

The cloud-based computing server system 104 may be configured to generate a series of notifications to improve the likelihood that it is received/viewed by the caregiver soon enough so that the care recipient can still take the medications on time. For example, the cloud-based computing server system 104 may initially generate a text/email/alert to the caregiver's computing device 106 and assess the latency in communication. If the prescribed medication schedule of the care recipient is about to expire and no additional movement has been detected from the computing device 102, the cloud-based computing server system 104 may initiate a call directly to the caregiver's computing device 106.

As discussed above, the computing device 102 may monitor the care recipient's access to one of the chambers based at least upon motion sensor measurements. In one embodiment, in order to save power consumption, the microcontroller of the computing device 102 may be configured to control the motion sensor to detect movements at a certain average frequency, with a high rate of sensing concentrated around the desired dosing times (e.g., morning, noon, and night). The microcontroller may implement a sleep mode or low power mode in accordance with the saved medication schedule of the care recipient. For example, the motion sensor(s) may be set to operate in a low power mode at a low sample rate, to conserve power. If the motion sensor detects a movement of the computing device 102, it may trigger an asynchronous interrupt to wake up the microcontroller, which may set the computing device 102 to an operational mode. In addition, the motion sensor may detect certain distortions or noise signals when the care recipient is handling the computing device 102 (e.g., removing medications from chambers or carrying the device 102 around). The microcontroller or the cloud-based computing server system 104 may receive and analyze these signals to adjust the sampling rate of the motion sensor to compensate.

In another embodiment, the cloud-based computing server system 104 may determine refill rates for respective medications of the care recipient and notify the caregiver via any suitable communication channels (a text message, automated phone call, email message, App alert, etc.).

In some implementations, each computing device 102 may have a device identifier that is assigned by the manufacturer and uniquely identifies the device. The device identifier may be provided to the server system 104 during registration of the care recipient, caregiver and the device. For example, the device identifier may include a factory-installed production signature of the microcontroller or other processing device inside the computing device 102. The device identifier may also include a phone number or static IP address associated with a communications module in the computing device 102. Data related or obtained by the computing device 102 may be associated with the unique device identifier and saved by the server system 104 on a suitable database device. Specifically, the server system 104 may maintain a list of device identifiers that are authorized to participate in the network environment in order to detect under-participation associated with a given device identifier, or participation by an unauthorized party.

In certain embodiments, real-time medical data, such as blood sugar or blood pressure, from devices such as wearable devises, may also be integrated with the medication adherence data collected and recorded in the server system 104 or an in-home personal health hub or a third party, such as a doctor, nurse, or other medical provider, to provide even more granular information regarding the care recipient's health. For example, blood sugar and/or blood pressure levels may be analyzed before and after blood sugar and/or blood pressure medication is taken as well as throughout the day. Health care providers may then learn the efficiency of the respective mediation and whether the medication needs to be changed. The caregiver may be configured to communicate with the server system 104 regarding the adjustment of the medication regime and schedule of the care recipient.

In some examples, the microcontroller of the computing device 102 may be reset externally by a user via a reset button. If the reset button is activated, various settings for the computing device 102 (audio/visual alarms, LED colors, etc.) are initialized to default settings. These settings may be controlled wirelessly by the computing device 106 and/or the server system 104 via the communication network 108 and communication protocols 110*a*, 110*b*, 110*c*.

The care recipient's medication schedule may be programmed directly into the memory of the microcontroller of the computing device 102. The schedule may be programmed into the firmware code of the microcontroller, for example. If the communication module of the computing device 102, such as the cellular module, is out of range for receiving a wireless signal, if there is no Internet or other network access, or if a new schedule has not been received, the medication schedule allows the computing device 102 to operate until it has returned within signal range or otherwise received an updated medication schedule.

The medication schedule may be updated by the server system 104 via one or more networks (such as the communication network 108). In some embodiments, the computing devices 102 and 106 may be configured to regularly retrieve the medication schedule of the care recipient from the server system 104 and save it on a local memory, such that the caregiver may monitor the medication adherence of the care recipient based on the up-to-date medication information. A display (not shown) may be provided on the computing device 102 to show a current time, and/or the time of the next dose.

In some embodiments, the server system 104 may determine whether a detected movement of the computing device 102 is indicative of medication removal from one of the chambers. For example, the motion sensor of the computing device 102 may obtain data indicating that a movement or orientation of the computing device 102 exceeds a threshold. The server system 104 may compare the detected event against a threshold amount of time to the next scheduled time of a medication of the care recipient. If the occurrence of the detected event is within the threshold, the server system 104 may increase the sampling rate of the motion sensor and obtain other data from the computing device 102 in order to confirm that the care recipient is taking a medication in accordance with a prescribed medication schedule.

The server system 104 may control the microcontroller of the computing device 102 to generate audio and/or visual signals to alert the care recipient because he/she has not taken a medication at the prescribed time or within the threshold amount of time. These signals may comprise various combinations of flashing lights of the LEDs and/or sounds, for example. Subsequently, the microcontroller may detect whether or not the care recipient has engaged a snooze button. The time to sound the alarm and/or the time to check for whether the snooze button has been engaged may be configured by the caregiver via his/her computing device 106 at the server system 104. This information may be stored by the server system 104, and then transmitted to the computing device 102 via the communication network 108. The motion sensor of the computing device 102 may then be configured to detect whether the care recipient is taking the medication in response to the alert signals, as discussed above. The microcontroller of the computing device 102 may store all the sensing data as they become available sequentially and transmit the sensing data along with other identifying information of the device or the care recipient to the server system 104.

The server system 104 may check the data received from a given computing device 102 which may include various sensor measurement data, the device identifier of the computing device 102 sending the data, as well as other data concerning the computing device 102, such as the state of the battery. The server system 104 may parse the sensed data for processing and storage in a corresponding database. In one embodiment, a timestamp may be used on the data in the database. The timestamp may be transmitted from the computing device 102 when the data is sent or may be recorded by the server system 104 when the data is received. The database of the server system 104 may use appropriate methods and data structures to associate the sensing data, device ID, and timestamp in a table, for example.

In another embodiment, the server system 104 may check whether the data value corresponding to the voltage on the battery received from the computing device 102 indicates a low level of charge, and thus needs recharging. The server system 104 may be configured to generate a notification signal to remind the caregiver or the care recipient to recharge the battery of the computing device 102 in response to detecting a low level of charge of the battery.

On the other hand, if no sensing data have been received from the computing device 102, the server system 104 may be configured to either request data transmissions from the computing device 102 in order to determine whether the medications have been removed from one of the chambers.

In accordance with some aspects of the present disclosure, the caregiver or one or more members of the care community of the care recipient may use a computing device 106 to access the system 100 and set up configurable alerts to monitor (e.g., text, phone, app alerts, etc.) medication adherence of a care recipient who is using the computing device 102 for medication management purposes. In one aspect, the caregiver may set up specific targets, people, methods, times via an App on his/her computing device 106. Further, the caregiver may set up configurable standards for accepting an interaction as valid.

In response to determining a medication non-adherence event has occurred, the server system 104 may log the event and notify the caregiver accordingly. The server system 104 may use various statistical and data analytics tools to provide a medication adherence for a specific care recipient over a period of time. In addition, the server system 104 may collect and analyze information received from a portion of the computing devices 102 deployed within the network and provide an overall population trends related to medication adherence, by insurance companies, pharmacies, and/or medical providers, or example.

In another aspect, the server system 104 may allow a caregiver to select a preferred communication method (e.g., phone calls, text messages, emails, App alerts, etc.). Each caregiver may also be able to select different types of notifications for different events (text message for charging reminder, phone call for medication reminder).

In accordance with an embodiment, the application downloaded and installed on the caregiver's computing device 106 may be configured to generate and display adherence and/or non-adherence indicators of a specific care recipient. For example, such indicators may show medication adherence and/or non-adherence of the specific care recipient during a selected period of time, most missed medication or dose over a time period. These adherence indicators are based on the number of times the microcontroller of the computing device 102 and/or the server system 104 determines that the care recipient opened at least one chamber of the computing device 102 on time.

The application on the caregiver's computing device 106 may also be configured to allow the caregiver to monitor multiple care recipients and computing devices 102 in accordance with, for example, patient identifiers and/or device identifiers.

Unless specifically stated otherwise as apparent from the foregoing disclosure, it is appreciated that, throughout the present disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to,"

"adapted/adaptable," "able to," "conformable/conformed to," etc. Those skilled in the art will recognize that "configured to" can generally encompass active-state components and/or inactive-state components and/or standby-state components, unless context requires otherwise.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

As used herein, the singular form of "a", "an", and "the" include the plural references unless the context clearly dictates otherwise.

As used herein, the term "comprising" is not intended to be limiting, but may be a transitional term synonymous with "including," "containing," or "characterized by." The term "comprising" may thereby be inclusive or open-ended and does not exclude additional, unrecited elements or method steps when used in a claim. For instance, in describing a method, "comprising" indicates that the claim is open-ended and allows for additional steps. In describing a device, "comprising" may mean that a named element(s) may be essential for an embodiment or aspect, but other elements may be added and still form a construct within the scope of a claim. In contrast, the transitional phrase "consisting of" excludes any element, step, or ingredient not specified in a claim. This is consistent with the use of the term throughout the specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. None is admitted to be prior art.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A system deployed within a Cloud-based communication network, the system comprising:

a first computing device configured to store medications of a care recipient in a plurality of chambers, monitor the care recipient's adherence to a medication schedule via at least one sensor, and transmit measurement data of the at least one sensor to a computing server system, wherein the computing server system is configured to:

store, maintain and update a medication list of the care recipient, wherein the medication list includes information relating to a brand name of a specific prescription, active ingredients, all ingredients of the medication including non-active ingredients which include binders and tablet coatings, contact details of a manufacturer of the medication, how to take the medication including what to do if a patient takes too much or miss a dose, information to consider before the patient uses the medication including possible interactions with other medication or substances, safe storage and disposal information, what can happen while the patient is taking the medication including side effects, what the medication is used for, and contraindications including reasons when not to take a medication, receive the measurement data of the at least one sensor, process the measurement data to determine whether one of the plurality of chambers has been opened for retrieval of the medications stored therein in accordance with the medication schedule of the care recipient, and in response to determining that the one of the plurality of chambers has not been opened for retrieval of the medications stored therein in accordance with the medication schedule of the care recipient, generate and transmit a notification signal to a second computing device to indicate a medication non-adherence event of the care recipient, wherein the second computing device comprises:

a non-transitory computer-readable storage medium configured to store an application program; and a processor coupled to the non-transitory computer-readable storage medium and configured to control a plurality of modules to execute instructions of the application program to receive the notification signal.

2. The system of claim 1, wherein the notification signal comprises at least one of a text message to the second computing device used by a caregiver of the care recipient, an automated phone call to the second computing device, an alert via the application, or an email message to the caregiver.

3. The system of claim 1, wherein the at least one sensor includes a motion sensor configured to measure X-Y-Z axis acceleration signals of the first computing device, and the computing server system is configured to process the X-Y-Z axis acceleration signals to determine whether the one of the plurality of chambers has been opened for retrieval of the medications stored therein in accordance with the medication schedule of the care recipient.

4. The system of claim 1, wherein the first computing device includes a series of switches for the plurality of chambers, wherein the series of switches are connected with a common bus bar.

5. The system of claim 1, wherein each of the plurality of chambers includes independent spring contacts, wherein spring contacts of the plurality of chambers are electrically connected.

6. The system of claim 1, wherein the first computing device includes at least one of a cellular module, a Wi-Fi module or a Bluetooth module configured to transmit signals to the computing server system.

7. The system of claim 1, wherein the first computing device includes a plurality of light-emitting diodes and at least one speaker to generate visual and audio signals.

8. A computer-implemented method, comprising:

storing, by a first computing device deployed within a Cloud-based communication network, medications of a care recipient in a plurality of chambers;

monitoring, by a processor of the first computing device, the care recipient's adherence to a medication schedule via at least one sensor;

transmitting, by the first computing device, measurement data of the at least one sensor to a computing server system deployed within the Cloud-based communication network;

storing, maintain, and updating, by the computing server system, a medication list of the care recipient, wherein the medication list includes information relating to a brand name of a specific prescription, active ingredients, all ingredients of the medication including non-active ingredients which include binders and tablet coatings, contact details of a manufacturer of the medication, how to take the medication including what to do if a patient takes too much or miss a dose, information to consider before the patient uses the medication including possible interactions with other medication or substances, safe storage and disposal information, what can happen while the patient is taking the medication including side effects, what the medication is used for, and contraindications including reasons when not to take a medication;

receiving, by the computing server system, the measurement data of the at least one sensor;

processing, by the computing server system, the measurement data to determine whether one of the plurality of chambers has been opened for retrieval of the medications stored therein in accordance with the medication schedule of the care recipient;

in response to determining that the one of the plurality of chambers has not been opened for retrieval of the medications stored therein in accordance with the medication schedule of the care recipient, generating and transmitting, by the computing server system, a notification signal to a second computing device to indicate a medication non-adherence event of the care recipient; and receiving, by the second computing device, the notification signal.

9. The computer-implemented method of claim 8, wherein the notification signal comprises at least one of a text message to the second computing device used by a caregiver of the care recipient, an automated phone call to the second computing device, an alert via the application, or an email message to the caregiver.

10. The computer-implemented method of claim 8, further comprising using a motion sensor of the at least one sensor to measure X-Y-Z axis acceleration signals of the first computing device, and processing, by the computing server system, the X-Y-Z axis acceleration signals to determine whether the one of the plurality of chambers has been opened for retrieval of the medications stored therein in accordance with the medication schedule of the care recipient.

11. The computer-implemented method of claim 8, wherein the first computing device includes a series of switches for the plurality of chambers, wherein the series of switches are connected with a common bus bar.

12. The computer-implemented method of claim 8, wherein each of the plurality of chambers includes independent spring contacts, wherein spring contacts of the plurality of chambers are electrically connected.

13. The computer-implemented method of claim 8, wherein the first computing device includes at least one of a cellular module, a Wi-Fi module or a Bluetooth module configured to transmit signals to the computing server system.

14. The computer-implemented method of claim 8, wherein the first computing device includes a plurality of light-emitting diodes and at least one speaker to generate visual and audio signals.

15. A non-transitory computer readable medium storing computer executable instructions for a system deployed in a Cloud-based communication network, the instructions being configured for:

storing, by a first computing device deployed within a Cloud-based communication network, medications of a care recipient in a plurality of chambers;

monitoring, by a processor of the first computing device, the care recipient's adherence to a medication schedule via at least one sensor;

transmitting, by the first computing device, measurement data of the at least one sensor to a computing server system deployed within the Cloud-based communication network;

storing, maintain, and updating, by the computing server system, a medication list of the care recipient, wherein the medication list includes information relating to a brand name of a specific prescription, active ingredients, all ingredients of the medication including non-active ingredients which include binders and tablet coatings, contact details of a manufacturer of the medication, how to take the medication including what to do if a patient takes too much or miss a dose, information to consider before the patient uses the medication including possible interactions with other medication or substances, safe storage and disposal information, what can happen while the patient is taking the medication including side effects, what the medication is used for, and contraindications including reasons when not to take a medication;

receiving, by the computing server system, the measurement data of the at least one sensor;

processing, by the computing server system, the measurement data to determine whether one of the plurality of chambers has been opened for retrieval of the medications stored therein in accordance with the medication schedule of the care recipient;

in response to determining that the one of the plurality of chambers has not been opened for retrieval of the medications stored therein in accordance with the medication schedule of the care recipient, generating and transmitting, by the computing server system, a notification signal to a second computing device to indicate a medication non-adherence event of the care recipient; and receiving, by the second computing device, the notification signal.

16. The non-transitory computer readable medium of claim 15, wherein the notification signal comprises at least one of a text message to the second computing device used by a caregiver of the care recipient, an automated phone call to the second computing device, an alert via the application, or an email message to the caregiver.

17. The non-transitory computer readable medium of claim 15, further comprising instructions configured for using a motion sensor of the at least one sensor to measure X-Y-Z axis acceleration signals of the first computing device, and processing, by the computing server system, the X-Y-Z axis acceleration signals to determine whether the one of the plurality of chambers has been opened for retrieval of the medications stored therein in accordance with the medication schedule of the care recipient.

* * * * *